United States Patent [19]

Keil et al.

[11] Patent Number: 5,696,283

[45] Date of Patent: Dec. 9, 1997

[54] PREPARATION OF METHYL ISOPROYLIDENEAMINOOXYACETOXYA-CETATE

[75] Inventors: Michael Keil, Freinsheim; Josef Wahl, Schifferstadt, both of Germany

[73] Assignee: BASF Aktiengesellschaft, Ludwigshafen, Germany

[21] Appl. No.: 545,910

[22] Filed: Oct. 19, 1995

[30] Foreign Application Priority Data

Oct. 22, 1994 [DE] Germany ............... 4437904.8

[51] Int. Cl.⁶ .................................. C07C 229/00
[52] U.S. Cl. .................................... 560/168
[58] Field of Search ........................ 560/168

[56] References Cited

U.S. PATENT DOCUMENTS 4,744,811  5/1988  Schulz et al. .

FOREIGN PATENT DOCUMENTS

| 1 259 629 | 9/1989 | Canada . |
| 023 560 | 2/1981 | European Pat. Off. . |
| 121 701 | 10/1984 | European Pat. Off. . |
| 158 159 | 10/1985 | European Pat. Off. . |
| 243 834 | 11/1987 | European Pat. Off. . |
| 89/11473 | 11/1989 | WIPO . |

OTHER PUBLICATIONS

Journal of General Chemistry of the USSR, vol 52, 1982 p. 204
Derwent Abstract of DE 2927117, Jul. 5, 1979.

Primary Examiner—Michael L. Shippen
Attorney, Agent, or Firm—Keil & Weinkauf

[57] ABSTRACT

Process for preparing methyl isopropylideneaminooxyacetoxyacetate I

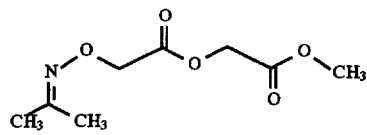

by reacting in an integrated process, a) acetone with hydroxylammonium sulfate and sodium hydroxide solution to give acetone oxime, the reaction being performed in the presence of toluene and/or the acetone oxime being extracted from the reaction mixture with toluene, b) treating the toluene solution thus obtained with sodium hydroxide solution and removing water, c) exchanging toluene for a dipolar aprotic solvent by distillation, d) reacting the crystal mash thus obtained with the sodium salt of chloroacetic acid to give the sodium salt of isopropylideneaminooxyacetic acid and then treating the reaction mixture with methyl chloroacetate and e) isolating the methyl isopropylideneaminooxyacetoxyacetate formed in d).

4 Claims, No Drawings

PREPARATION OF METHYL ISOPROYLIDENEAMINOOXYACETOXYACETATE

BACKGROUND OF THE INVENTION

1. Field of the Invention

The present invention relates to a process for preparing methyl isopropylideneaminooxyacetoxyacetate of the formula I

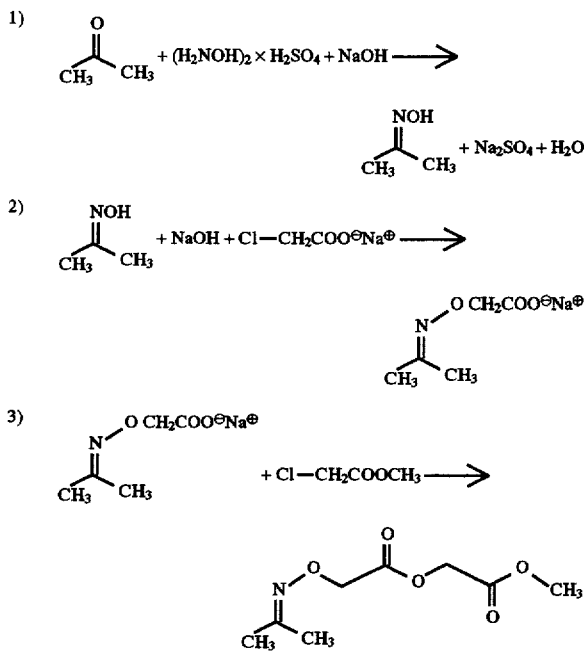

Compound I is used as a bioregulator for lowering the endogenous ethylene level in plants (EP-A 243 834).

2. Description of the Related Art

According to the prior art, compound I can be obtained via the individual steps 1) to 3) shown in the following scheme.

The preparation of acetone oxime is described, for example, in Houben-Weyl, Methoden der Organischen Chemie. [Methods of Organic Chemistry], Vol. 10/4, 1968, p. 58. The alkylation with Na chloroacetate is disclosed in Zhurn. Obshch. Khim. 52 (1), 1982, 223 and in WO 89/11473 and EP-A 158 159. The subsequent alkylation with methyl chloroacetate can be taken from EP-A 243 834.

The conversion of the 3 steps described to an economical process in the production of large amounts, however, includes the following difficulties:

1. The isolation and purification of the intermediates by filtration or distillation is laborious and expensive. The total yield over all steps is unsatisfactory.

2. The alkylation of acetone oxime in protic solvents (Zhurn. Obshch. Khim. 52 (1), 223 and EP-A 121 701) only proceeds in unsatisfactory yields; the reactions in aprotic solvents described (EP-A 158 159 and WO 89/11473) necessitated a large excess of oxime.

There is therefore a need for a simple process in which purification steps of intermediates can be dispensed with, an excess of acetone oxime can be dispensed with, all steps can in principle be carried out in one reaction vessel.

Associated with the realization of these requirements would be a lower outlay in terms of apparatus, a more favorable total yield and thus a higher economy.

SUMMARY OF THE INVENTION

Accordingly, a process for preparing methyl isopropylideneaminooxyacetoxyacetate of the formula I

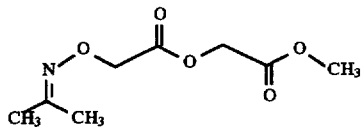

has now been found, which comprises reacting in an integrated process, without isolation of intermediates, a) acetone with hydroxylammonium sulfate and sodium hydroxide solution to give acetone oxime, the reaction being performed in the presence of toluene and/or the acetone oxime being extracted from the reaction mixture with toluene, b) treating the toluene solution thus obtained with sodium hydroxide solution and removing water, c) exchanging toluene for a dipolar aprotic solvent by distillation, d) reacting the crystal mash thus obtained with the sodium salt of chloroacetic acid to give the sodium salt of isopropylideneaminooxyacetic acid and then treating the reaction mixture with methyl chloroacetate and e) isolating the methyl isopropylideneaminooxyacetoxyacetate.

DESCRIPTION OF THE PREFERRED EMBODIMENTS

The first reaction step (step a)) in the one-pot process according to the invention is carried out in a manner known per se in aqueous medium and the acetone oxime is then extracted from the reaction mixture with toluene or the reaction is advantageously already performed in the presence of toluene. In this case the amount of toluene is expediently from approximately 150 to 900 ml, based on 1 mol of acetone oxime formed.

The reaction mixture thus obtained is treated with sodium hydroxide solution without further purification. If the reaction procedure is arranged in this way surprisingly high excesses of acetone oxime are not necessary for the subsequent methylation. Instead, it has proven advantageous to add approximately equimolar amounts of sodium hydroxide solution, ie. from approximately 1.0 to 1.5 mol, in particular from 1.0 to 1.2 mol, based on acetone oxime.

Water of reaction resulting during salt formation and water entrained by sodium hydroxide solution are removed from the reaction mixture azeotropically during the reaction or after it, for example at from 50° to 110° C. and from 100 mbar to 1 bar.

A solvent exchange is then performed, eg. by treating the toluene suspension with a suitable dipolar aprotic solvent such as N-methylpyrrolidone or in particular dimethylformamide, which can begin to dissolve the acetone oxime Na salt better and cause it to react. At the same time or subsequently, toluene is removed by distillation.

The amount of dipolar aprotic solvent added expediently corresponds to the amounts of toluene distilled off, ie. is approximately from 150 to 900 ml per mole of acetone oxime Na salt.

The crystal mash thus obtained is reacted in the next step (step d)) first with the sodium salt of chloroacetic acid (approximately 1 mol equivalent) and the product I is then formed from the sodium salt of isopropylideneaminoacetic acid using methyl chloroacetate. The first reaction step is performed, for example, at from 20° to 150° C., in particular from 50° to 100° C. For the last reaction step, temperatures from 20° to 150° C., in particular from 50° to 80° C., have proven expedient. The reaction components can be present in approximately stoichiometric amount, ie. amounts from 1 to 1.2 mol per mole of Na salt. A higher excess of one reaction component or the other would be possible, but hardly economical.

The useful product I can be removed from the reaction mixture in a manner known per se. The following work-up has proven particularly expedient: the solvent is distilled off at from 50° to 80° C. and 20 to 200 mbar, the residue is taken up in toluene, and the mixture is washed with water and fractionally distilled.

The following example illustrates the process claimed. The total yield achieved is surprisingly high and the experimental procedure significantly simpler than the steps in the stepwise preparation of the intermediates.

EXAMPLE

Preparation of methyl isopropylideneaminooxyacetoxyacetate 980 ml of water, 328 g of hydroxylammonium sulfate and 460 ml of toluene are initially introduced at from 20° to 50° C. and 232 g (4 mol) of acetone and 320 g (4 mol) of conc. sodium hydroxide solution are simultaneously added dropwise at pH 4.5 to 5.0. To complete the reaction, the mixture is stirred for about ½ hour and the phases are separated at from 30° to 40° C. The water phase is extracted twice by shaking with 460 ml of toluene. The entire organic phase is refluxed under reduced pressure (55° C.) at 100–200 mbar. For salt formation, 320 g (4 mol) of conc. sodium hydroxide solution are added dropwise and 250 g of water are simultaneously removed. Toluene is then distilled off at the same temperature and 2,000 ml of DMF are added. 466 g (4 mol) of Na chloroacetate are added to the crystal mash at 50° C. in portions and the mixture is stirred at 50° C. for 5 hours. 433 g (4 mol) of methyl chloroacetate are then added dropwise at from 50° to 55° C., stirring of the mixture is continued at 55° C. for 10 hours and DMF is then distilled over at the same temperature and under reduced pressure.

The residue is taken up in toluene and washed with water. After a fractional distillation at 100° C./0.2 mm Hg, 531 g of final product are obtained. This corresponds to a total yield over all stages of 65.3% of theory. The product is obtained in a GC purity of 99.9% and has a refractive index $n_D^{20}$ of 1.4469.

Comparative examination of literature yields

The preparation of acetone oxime takes place in about 90% yield. The alkylation with Na chloroacetate is described in 49% yield (Zhurn. Obshch. Khim. 52 (1), 223). In the similar processes in WO 89/11473 and EP-A 158 159, yields of around 80% are indeed achieved, but only using a large excess of oxime. The second alkylation step is carried out with ethyl bromoacetate according to EP-A 234 834 in 75% yield.

We claim:

1. A process for preparing methyl isopropylideneaminooxyacetoxyacetate of the formula I

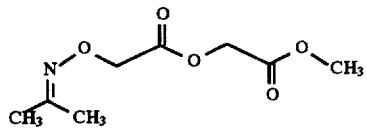

which comprises reacting in an integrated process
a) acetone with hydroxylammonium sulfate and sodium hydroxide solution to give acetone oxime, the reaction being performed in the presence of toluene and/or the acetone oxime being extracted from the reaction mixture with toluene,
b) treating the toluene solution thus obtained with sodium hydroxide solution and removing water,
c) exchanging toluene for a dipolar aprotic solvent by distillation,
d) reacting the crystal mash thus obtained with the sodium salt of chloroacetic acid to give the sodium salt of isopropylideneaminooxyacetic acid and then treating the reaction mixture with methyl chloroacetate and
e) isolating the methyl isopropylideneaminooxyacetoxyacetate formed in step d).

2. The process of claim 1, wherein the acetone oxime is reacted with approximately equimolar amounts of sodium hydroxide solution.

3. The process of claim 1, wherein the dipolar aprotic solvent used in step c) is dimethylformamide.

4. The process of claim 1, wherein the compound I is isolated from the reaction mixture by distilling off the solvent, treating the residue with toluene, washing with water and distilling.

* * * * *